United States Patent
Mick

(10) Patent No.: US 7,666,130 B2
(45) Date of Patent: Feb. 23, 2010

(54) SPLIT-RING BRACHYTHERAPY DEVICE AND METHOD FOR CERVICAL BRACHYTHERAPY TREATMENT USING A SPLIT-RING BRACHYTHERAPY DEVICE

(75) Inventor: Felix W. Mick, Bronxville, NY (US)

(73) Assignee: Mick Radio-Nuclear Instruments, Inc., Mt. Vernon, NY (US)

( * ) Notice: Subject to any disclaimer, the term of this patent is extended or adjusted under 35 U.S.C. 154(b) by 0 days.

(21) Appl. No.: 11/821,285

(22) Filed: Jun. 21, 2007

(65) Prior Publication Data
US 2008/0064916 A1 Mar. 13, 2008

Related U.S. Application Data

(60) Provisional application No. 60/815,696, filed on Jun. 21, 2006.

(51) Int. Cl.
*A61N 5/00* (2006.01)
(52) U.S. Cl. ......................................................... 600/6
(58) Field of Classification Search ................. 600/1–7; 604/505
See application file for complete search history.

(56) References Cited

U.S. PATENT DOCUMENTS

| | | | | | |
|---|---|---|---|---|---|
| 3,750,653 | A | * | 8/1973 | Simon | 600/6 |
| 4,294,264 | A | * | 10/1981 | Fischell et al. | 600/591 |
| 4,434,789 | A | * | 3/1984 | Kumar | 600/6 |
| 5,012,357 | A | * | 4/1991 | Schoeppel et al. | 378/65 |
| 5,084,001 | A | * | 1/1992 | Van't Hooft et al. | 600/3 |
| 6,699,171 | B2 | * | 3/2004 | Harmon | 600/6 |
| 7,041,048 | B2 | * | 5/2006 | Drobnik et al. | 600/7 |
| 2003/0191391 | A1 | * | 10/2003 | Burbank et al. | 600/453 |
| 2006/0235260 | A1 | * | 10/2006 | Mourtada et al. | 600/7 |

OTHER PUBLICATIONS

International Search Report and Written Opinion for PCT/US2007/014658, dated Apr. 4, 2008.

* cited by examiner

*Primary Examiner*—Samuel G Gilbert
(74) *Attorney, Agent, or Firm*—Kenyon & Kenyon LLP

(57) ABSTRACT

Methods and devices are for providing the delivery of radioactive therapeutics to a cervix using a split ring applicator. The split ring applicator includes a central tandem and a plurality of adjustable split ring tubes that are adjustable laterally in relation to a cervical axis. A radiation dosage is deliverable to a cervical wall by at least one of the plurality of adjustable split ring tubes.

32 Claims, 21 Drawing Sheets

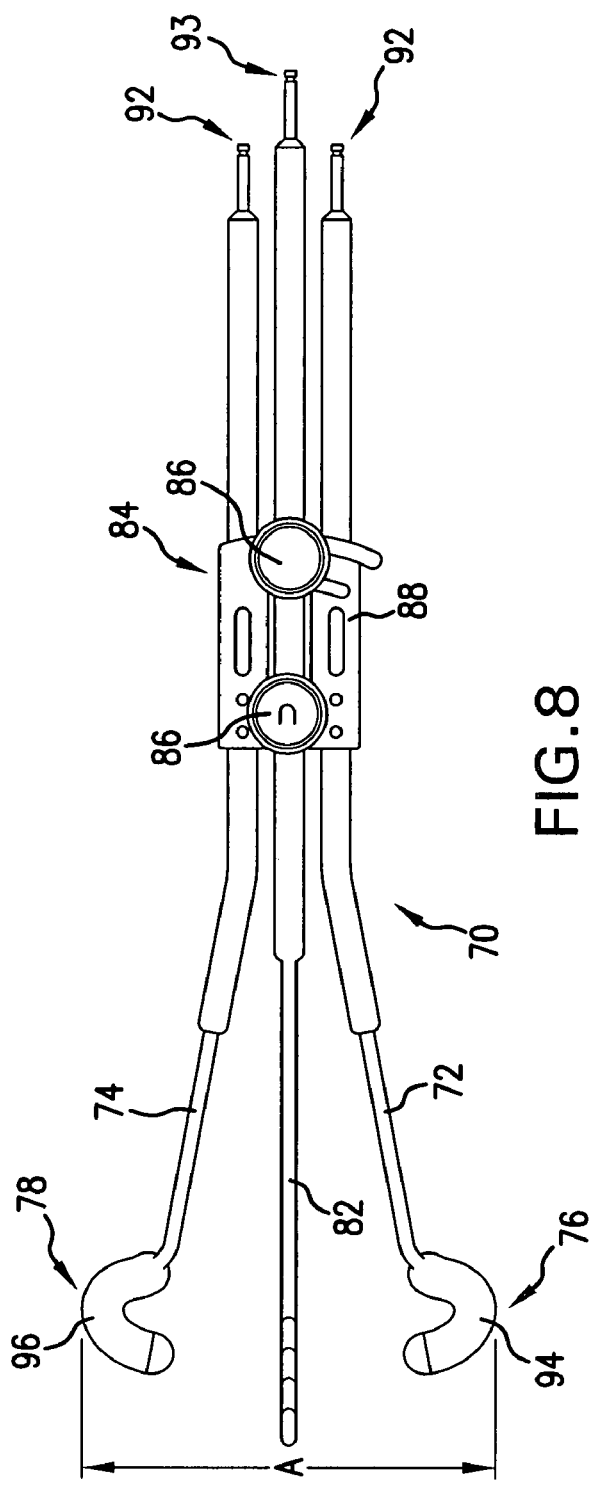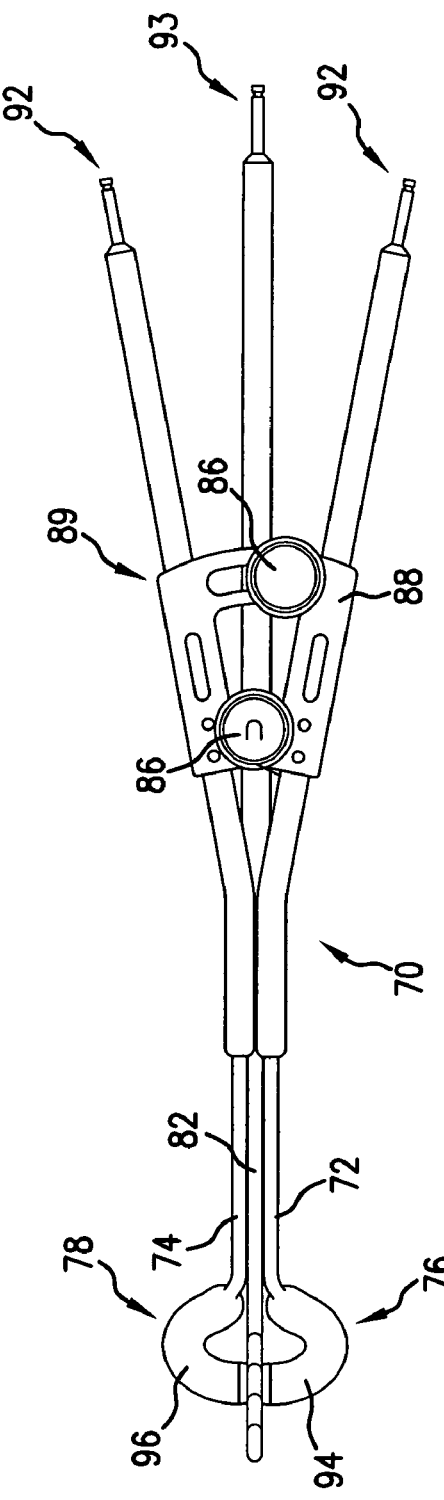
FIG.8
FIG.9

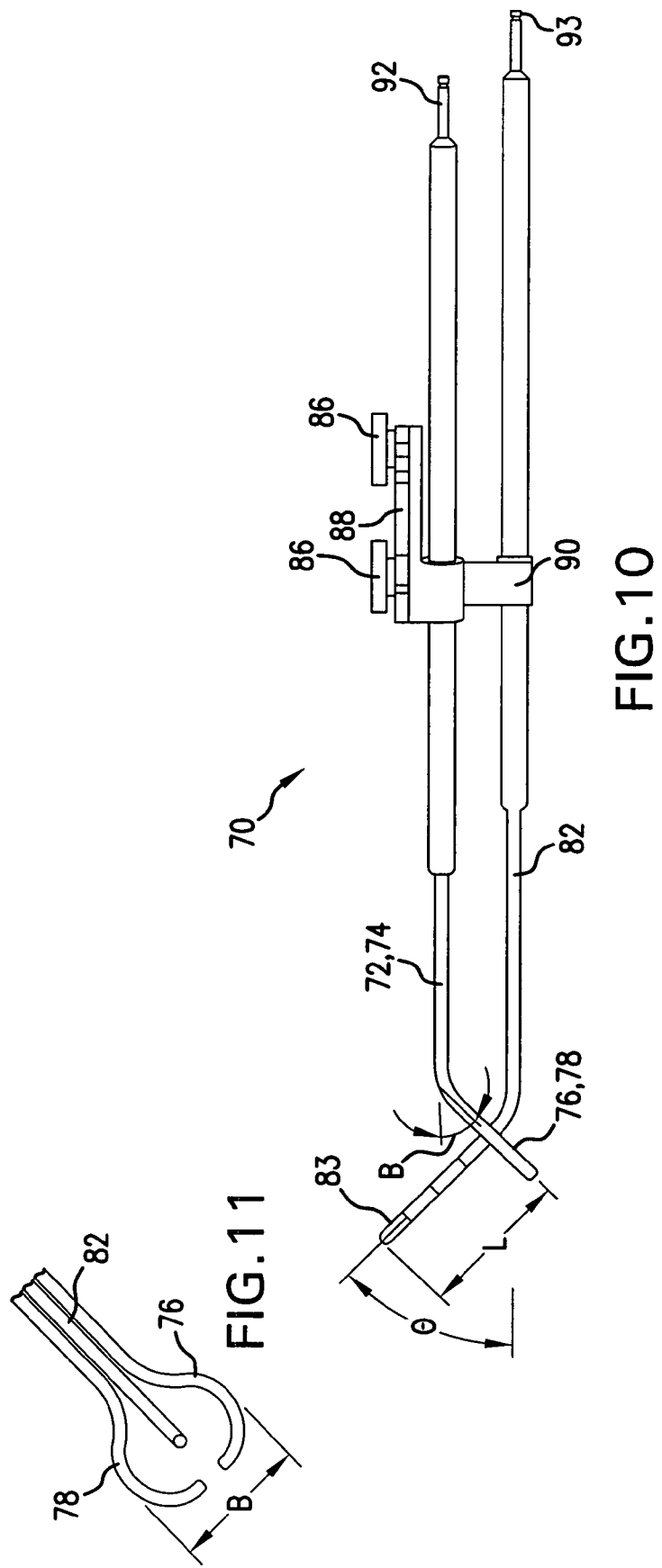

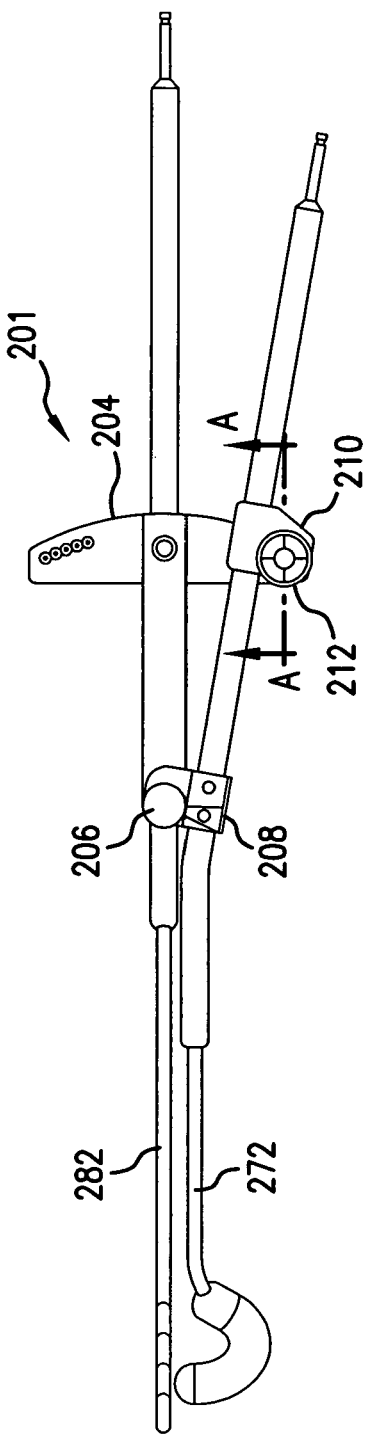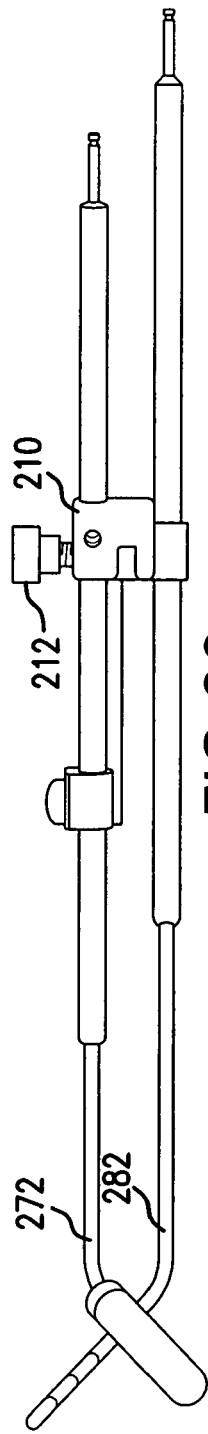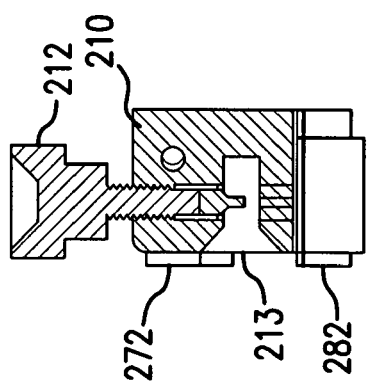

SPLIT-RING BRACHYTHERAPY DEVICE AND METHOD FOR CERVICAL BRACHYTHERAPY TREATMENT USING A SPLIT-RING BRACHYTHERAPY DEVICE

CROSS-REFERENCE TO RELATED APPLICATIONS

The present application claims the benefit of U.S. Provisional Patent Application No. 60/815,696, filed on Jun. 21, 2006, which is expressly incorporated herein in its entirety by reference thereto.

FIELD OF THE INVENTION

The present invention relates generally to a split-ring brachytherapy device and to a method for cervical brachytherapy treatment using a split-ring brachytherapy device. Radioactive therapeutics may be delivered to a region of the cervix, e.g., to provide for treatment of cervical cancerous tissue.

BACKGROUND INFORMATION

Brachytherapy is a form of cancer treatment in which radiation sources are placed inside a patient's body, e.g., to irradiate a tumor. In brachytherapy, a physician typically implants several radioactive seeds in or around a tumor, thereby providing a higher radiation dose to the tumor than would be possible with external beam radiation therapy. Careful placement of the radioactive seeds is critical to allow for localized and precise irradiation of the tumor.

Cervix applicators using radiation in the treatment of cervical cancer have been in existence since the discovery of Radium in the early 19th century. Historically, Radium sources (sealed sources) were placed in ovoids attached to tubes and thereafter inserted "manually" into vaginal or intrauterine cavities for the treatment of cancer. The insertion of the applicator was associated with significant radiation exposure to the physicians handling the apparatus.

Henschke et al. at Memorial Hospital in New York is believed to have introduced the "Afterloading Technique" in 1960, in which applicators are inserted first and the radioactive materials thereafter. Other isotopes, such as cesium-137 and iridium-192 sources have slowly replaced Radium. Cervix applicators have been developed in many different versions, and one widely accepted today is the Fletcher-Suit-Delclos (FSD) applicator. This applicator consists of two lateral ovoids and one central tandem. The ovoids can be spread laterally and fixed in place. The tandem is floating, and packing is required. Applicators in use today are considered "manual afterloading applicators".

In the early 1980s, High-Dose-Rate (HDR) Remote Afterloading is believed to have been introduced in the United States. These units provided greater protection from radiation exposure to staff and personnel. Applicators were inserted "cold" in specially shielded rooms, and the radioactive sources were inserted "remotely" from control consoles located outside the treatment room. The HDR break-through featured sealed sources much smaller in size than radium or cesium sources and opened new treatment possibilities and with it new opportunities in applicator designs.

SUMMARY

According to an example embodiment of the present invention, an applicator device for brachytherapy treatment of cervical cancer includes: a plurality of split ring tubes adjustable laterally to a cervical axis, each split ring tube adapted to deliver a radiation dosage to a cervical wall.

Each split ring tube may include a substantially straight proximal portion and generally semi-circular distal portion.

The device may include a central tandem attachable to the split ring tubes.

The device may include a coupling device adapted to couple the split ring tubes and the central tandem.

The central tandem may be rigidly attached to the coupling device.

The split ring tubes may be selectively lockable in position by the coupling device.

The device according may include a build-up cap disposed about a distal end of the split ring tube.

The build-up caps may have a thickness between about 5 mm and about 7.5 mm.

The build-up caps may be formed of silicon rubber.

Distal ends of the split ring tubes may be substantially semi-circular that form a substantially complete circular ring when the split ring tubes are in a closed position The ring may have a diameter of between about 20 mm and about 40 mm.

The central tandem may have an angled distal end section, an angle of the angled distal end section may be between about 30° and about 60° from a central axis of the central tandem, and the angled end section may be arranged approximately in a center of a ring formed by semi-circular rings of the split ring tubes.

The angled distal end section of the central tandem may have a length of between about 20 mm and about 80 mm.

The ring may be disposed at an angle between about 30° and about 60° from a planar surface formed by a central axis of the ring tubes.

The split ring tubes may be laterally displaceable such that outer most surfaces of distal ends of the split ring tubes are at a distance of between about 60 mm and about 80 mm.

The device may include a rectal retractor.

The applicator may be steam sterilizable, ETO sterilizable and/or gamma sterilizable.

A proximal end of each split ring tube may include a connector adapted to connect to a high dose rate afterloader device to deliver the radiation dosage into the split ring tube.

According to an example embodiment of the present invention, a brachytherapy treatment system for treatment of cervical cancer may include: a split ring applicator including a plurality of split ring tubes adjustable laterally to a cervical axis, each split ring tube adapted to deliver a radiation dosage to a cervical wall; and a high dose rate afterloader adapted to deliver the radiation dosage into at least one of the split ring tubes.

The system may include a central tandem attachable to the split ring tubes, and the high dose rate afterloader may be adapted to deliver the radiation dosage into the central tandem.

According to an example embodiment of the present invention, a method for treating cervical cancer includes: inserting a split ring applicator into a cervix, the applicator including a central tandem and a plurality of laterally adjustable split ring tubes; adjusting a lateral spacing between the split ring tubes; and applying a radioactive treatment to a cervical wall from the at least one of the split ring tubes.

The radioactive treatment may be applied in the applying step to the cervical wall by inserting a radioactive source into at least one of the split ring tubes.

The method may include locking the split ring tubes in a lateral spacing between the split ring tubes during a treatment time.

The method may include: unlocking the split ring tubes after the treatment time has elapsed; reversing the adjustment of the split ring tubes in the lateral direction; and removing the split ring applicator from the cervix.

The method may include: attaching an adjustable rectal retractor to the split ring applicator; retracting a rectum away from the split ring tubes by the rectal retractor; and locking the rectal retractor in place after the retracting step.

According to an example embodiment of the present invention, a method includes: inserting a central tandem of a split ring applicator into a uterine canal, the split ring applicator including at least a first split ring lateral tube and a second split ring lateral tube, the first split ring lateral tube and the second split ring lateral tube spreadable within at least one vaginal fornix; sliding the first split ring lateral tube of the split ring applicator in a direction substantially parallel to an axis of the central tandem, the first split ring lateral tube fixable in place thereafter to a coupling device, the coupling device connectable to the central tandem and lockable onto the central tandem by a first locking arrangement; sliding the second split ring lateral tube of the split ring applicator in a direction substantially parallel to the axis of the central tandem, the second split ring lateral tube lockable onto the coupling device; spreading at least one of the first split ring lateral tube and the second split ring lateral tube of the split ring applicator to a desired location within the at least one vaginal fornix; and fixing the at least one of the first split ring lateral tube and the second split ring lateral tube in place by a second locking arrangement.

At least one of (a) the first split ring lateral tube and (b) the second split ring lateral tube may be adapted to at least one of (a) a clinical condition and (b) an anatomical treatment condition.

Example embodiments of the present invention may provide a split ring applicator for the treatment of cervical cancer. The split ring applicator may provide physicians with certain advantages, e.g., increased flexibility, better optimization capabilities, etc. For example, splitting a ring of an applicator may permit a radiation dose to be spread laterally at specific points in the ring, e.g., to produce a more desirable isodose distribution which may not be achievable with a fixed ring applicator or a split spherical (ovoid) applicator. Additionally, rectal retractors may be part of the design to reduce the radiation dose to a rectal wall (by increasing the distance between sources and organs). These added features may enhance the delivery of the prescribed radiation dose to the cervix and specific target areas respectively, while reducing complications, including damage to healthy tissues.

An applicator may include a central tandem and a plurality of adjustable split ring tubes that are adjustable laterally in relation to a cervical axis. The central tandem and the adjustable split ring tubes may be connected via a coupling device. A radiation dosage is deliverable to a cervical wall by at least one of the plurality of adjustable split ring tubes. The plurality of adjustable split ring tubes may include build-up caps of varying thicknesses and may be constructed having various ring size diameters. The applicator may also have a rectal retractor. The applicator may be steam sterilized or sterilizable, ETO (ethylene oxide) sterilized or sterilizable, gamma sterilized or sterilizable, etc.

A method for treating cervical cancer may include: inserting a split ring applicator in a cervix, the split ring applicator including a central tandem and a plurality of laterally adjustable split ring tubes; adjusting at least one of the split ring tubes in a lateral direction; and applying a radioactive treatment to a cervical wall from at least one of the split ring tubes. The radioactive treatment may be applied to the cervical wall by inserting a radioactive source in at least one of the plurality of adjustable split ring tubes. The method may further include: locking the split ring applicator during a treatment time by at least one locking arrangement; unlocking at least one locking arrangement after the treatment time has passed; reversing the adjustment of the split ring tubes in the lateral direction; and removing the split ring applicator from the cervix. Additionally, the method may include: attaching an adjustable rectal retractor to the split ring applicator; adjusting the adjustable rectal retractor; and locking the adjustable rectal retractor in place by another locking arrangement. In the aforementioned method, the plurality of adjustable split ring tubes may be exactly two adjustable split ring tubes, and both of the split ring tubes may be adjusted in the lateral direction.

A method for treating cervical cancer may include: inserting a central tandem of a split ring applicator into a uterine canal, the split ring applicator including at least a first split ring lateral tube and a second split ring lateral tube, the first split ring lateral tube and the second split ring lateral tube spreadable within at least one vaginal fornix; sliding the first split ring lateral tube of the split ring applicator in parallel to an axis, the first split ring lateral tube fixable in place thereafter to a coupling device, the coupling device connectable to the central tandem and lockable onto the central tandem by a first locking arrangement; sliding the second split ring lateral tube of the split ring applicator in parallel to the axis, the second split ring lateral tube lockable onto the coupling device; spreading at least one of the first split ring lateral tube and the second split ring lateral tube of the split ring applicator to a desired location within the at least one vaginal fornix; and fixing the at least one of the first split ring lateral tube and the second split ring lateral tube in place by a second locking arrangement. At least one of the first split ring lateral tube and the second split ring lateral tube may be tailored to at least one of a clinical condition and an anatomical treatment condition.

Example embodiments of the present invention are described in more detail below with reference to the appended Figures.

BRIEF DESCRIPTION OF THE DRAWINGS

FIG. 8 is a plan view of the split ring applicator illustrated in FIG. 6 in an open position and including build-up caps.

FIG. 9 is a plan view of the split ring applicator illustrated in FIG. 6 in a closed position and including build-up caps.

FIG. 10 is a side view of the split ring applicator illustrated in FIG. 9 without build-up caps.

FIG. 11 is a plan view of a portion of the split ring applicator illustrated in FIG. 10.

FIG. 21 is a plan view of a split ring applicator according to an example embodiment of the present invention.

FIG. 22 is a side view of the split ring applicator illustrated in FIG. 21.

FIG. 23 is a cross-sectional view of the split ring applicator taken along the line A-A illustrated in FIG. 21.

DETAILED DESCRIPTION

Figure 1:
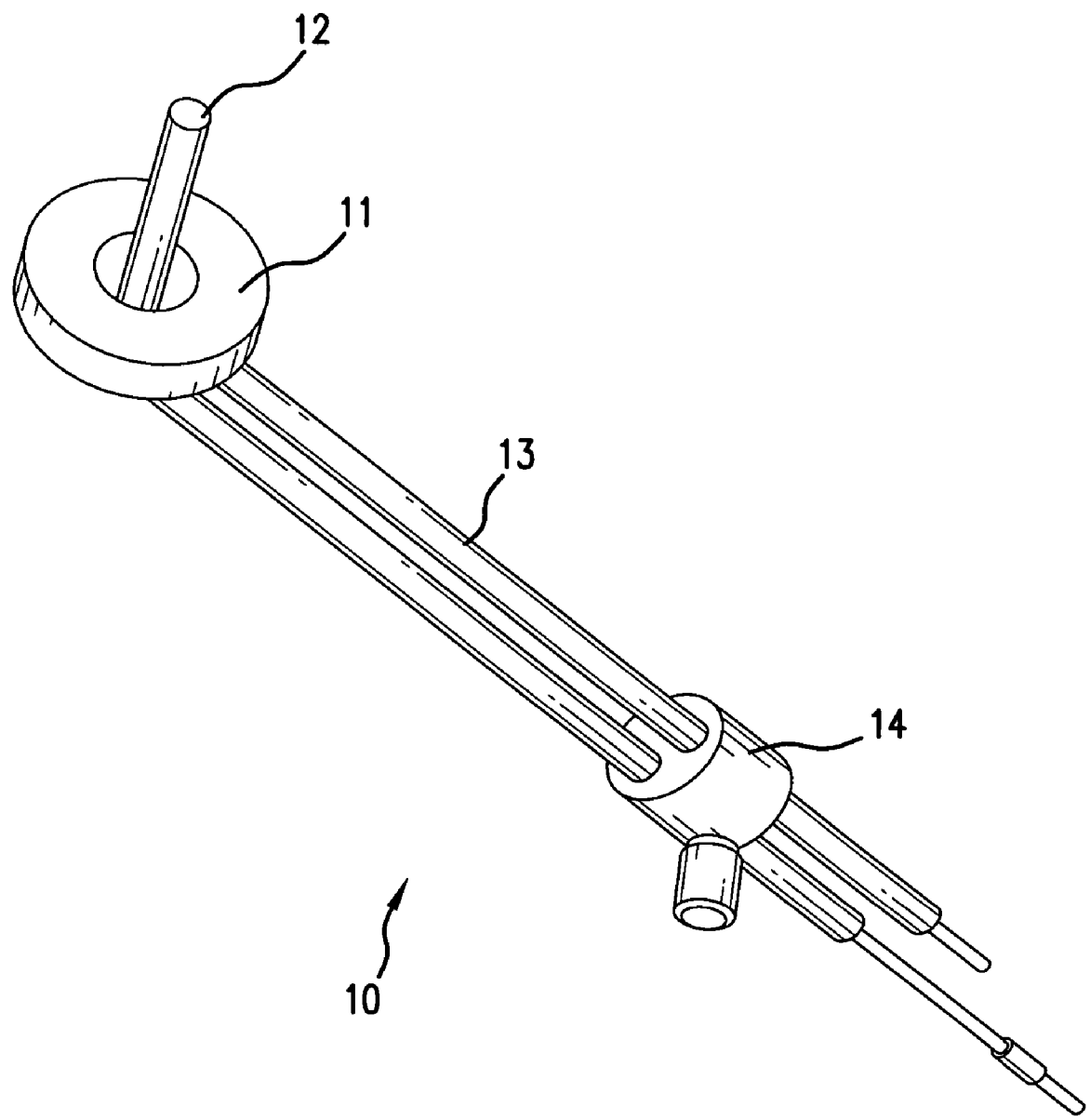
FIG. 1 illustrates a conventional ring applicator.

Like reference characters denote like parts in the several drawings.

FIG. 1 illustrates a conventional ring applicator 10 for use in intracavity application of radioactive materials. The ring applicator 10 includes ring 11, tandem 12, stalk (or post) 13 and connecting unit 14. The ring applicator 10 is designed for insertion into a cervix, generally after the cervix has been dilated through the use of an appropriate pharmaceutical. After ring applicator 10 has been inserted into the cervix, connecting unit 14 is adjusted to provide radiation, generally from iridium-192, at ring 11.

Figure 2:
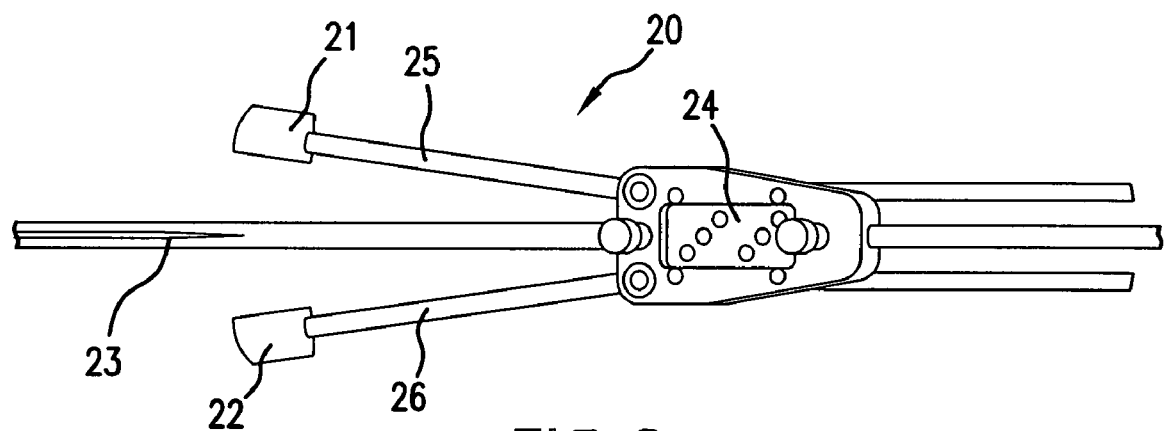
FIG. 2 illustrates a conventional split spherical applicator.

FIG. 2 illustrates a conventional split spherical applicator 20, also for intracavity application of radioactive materials. The split spherical applicator 20 includes ovoids 21, 22, split colpostats 25, 26, central tandem 23 and a connector 24. Connector 24 provides a pivot point for the movement of split colpostats 25, 26 and ovoids 21, 22. The use of split spherical applicator 20 is believed to have been limited to point source configurations in the ovoids and point source and axial limitations in both the ovoids and tandems. Split component applicators with varying geometry or radiation source placement for cervical treatments are not believed to be conventional.

Figure 3:
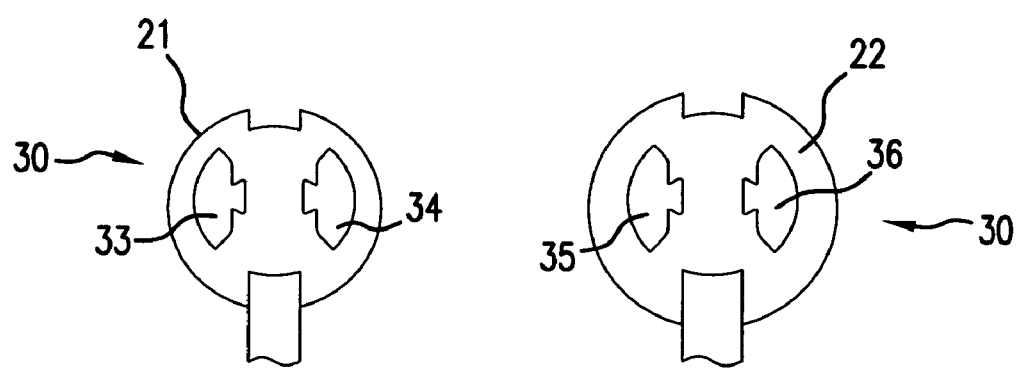
FIG. 3 illustrates end sections of the conventional split spherical applicator illustrated in FIG. 2.

FIG. 3 illustrates end sections 30 of ovoids 21, 22 of the device illustrated in FIG. 2. Outer diameters 31, 32 of the circumference of the ovoids is shown. Additionally, each ovoid 21, 22 includes two anterior and two posterior inward radiation shields 33, 34, 35, 36.

Figure 4:
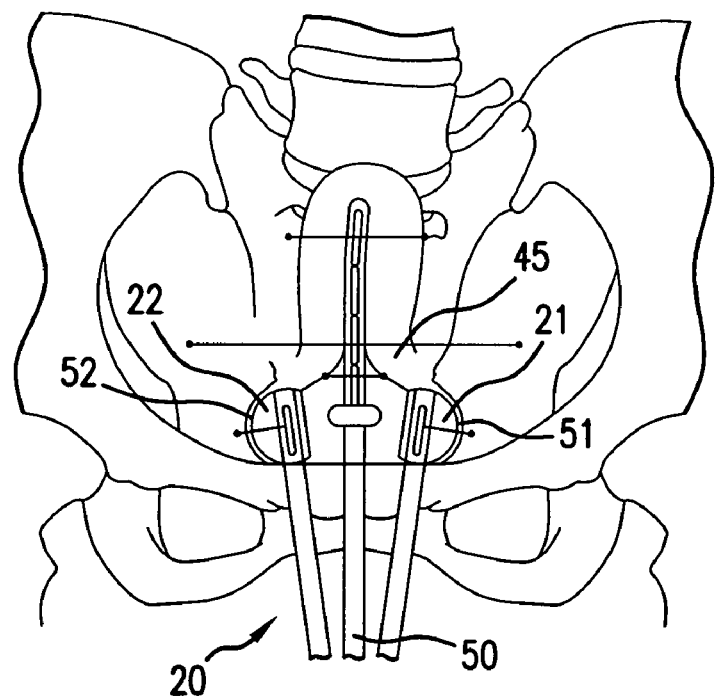
FIG. 4 is an anatomical cross-sectional view of the pelvic area from the front with the conventional split spherical applicator illustrated in FIG. 2 inserted in the cervix.

FIG. 4 is an anatomical cross-sectional view of the pelvic area from the front with the split spherical applicator 20 illustrated in FIG. 2 inserted in a cervix 45. Also shown in FIG. 4 is tandem 50 which provides a reference position and from which ovoids 21, 22 are adjusted toward right fornix 51 and left fornix 52.

Figure 5:
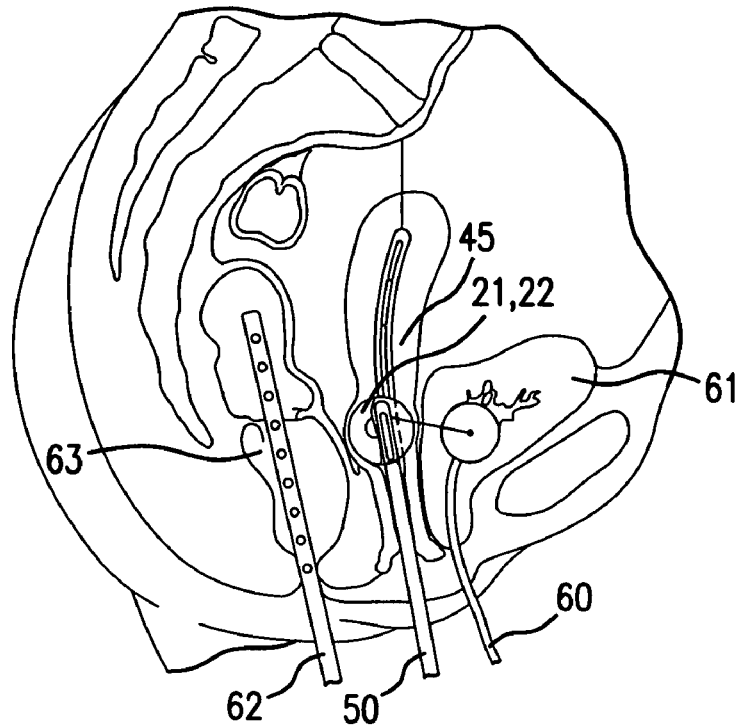
FIG. 5 is an anatomical cross-sectional view of the pelvic area from the side with the conventional split spherical applicator illustrated in FIG. 2 inserted in the cervix.

FIG. 5 is an anatomical cross-sectional view of the pelvic area from the side with the split spherical applicator 20 illustrated in FIG. 2 inserted in cervix 45. FIG. 5 illustrates tandem 50 as well as a bladder retractor 60 inserted in the urethra and positioned under the bladder 61 to move bladder 61 away from ovoids 21, 22. Also illustrated in FIG. 5 is rectal retractor 62 positioned above rectum 63. Rectal retractor 62 is inserted in the rectum and moves rectum 63 away from ovoids 21, 22.

Figure 6:
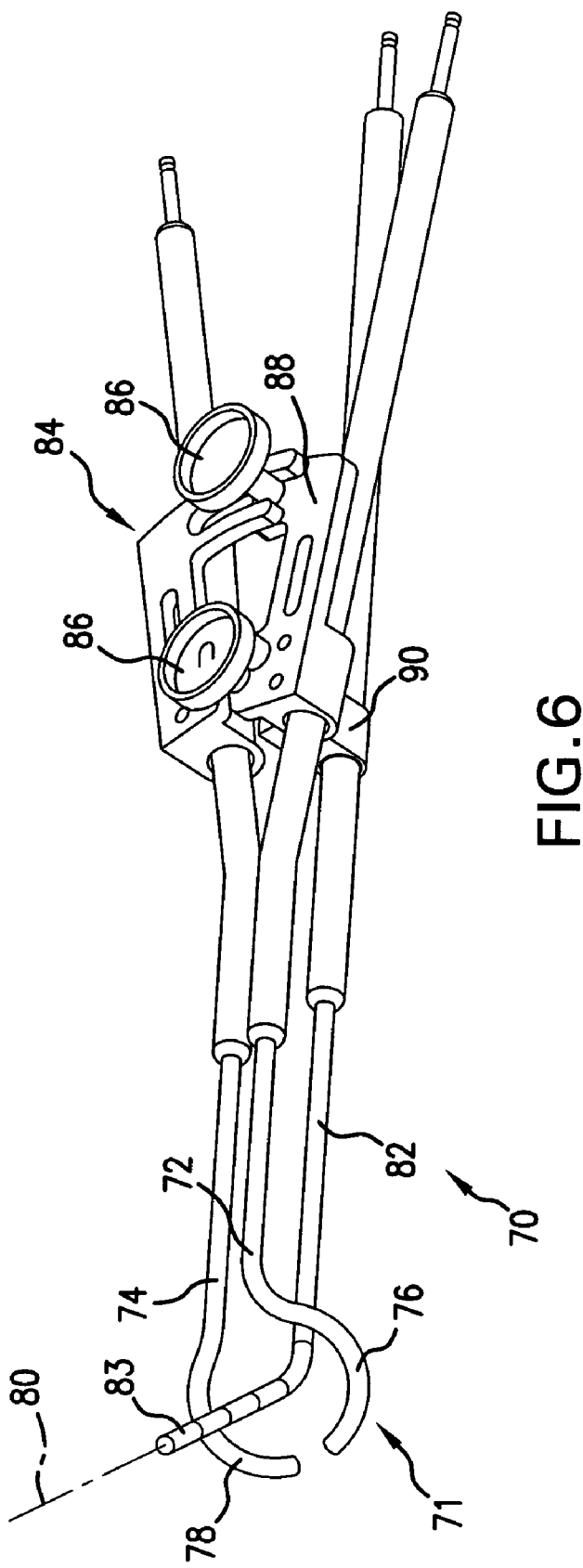
FIG. 6 is a perspective view of a split ring applicator according to an example embodiment of the present invention.

FIGS. 6 is a perspective view of a split ring applicator 70 according to an example embodiment of the present invention. Split ring applicator 70 includes adjustable split ring tubes 72, 74 (a left colpostat and a right colpostat), a central tandem 82 and a universal connector 84 (a coupling device) that connects adjustable split ring tubes 72, 74 and central tandem 82. Semi-circular rings 76, 78 form the distal ends of adjustable split ring tubes 72, 74. Universal connector 84 includes lock nuts 86 and adjustable brackets 88 so that the relative positioning of the semi-circular rings 76, 78 and tandem 82 may be provided and secured. Central tandem locator 90 is formed as a part of central tandem 82 and connects to universal connector 84. Central tandem locator 90 positions central tandem 82 such that central tandem end section 83 is central to semi-circular rings 76, 78. Central tandem end section 83 may be provided with a diameter of, e.g., 3 mm, which may be small enough to eliminate the need to dilate the cervix. Central tandem 82 may be rigidly attached to universal connector 84 such that it does not "float" and packing is not required during use of the split ring applicator 70. Adjustable split ring tubes 72, 74 are adjustable laterally to a cervical axis 80 through adjustable brackets 88 and may be locked in place by lock nuts 86. Adjustable split ring tubes 72, 74 may be selectively locked in one of multiple positions. A scale may be provided for determining or selecting the position. A radiation dose is deliverable, e.g., via an HDR after loader, to a cervical wall by at least one of the adjustable split ring tubes 72, 74. More or fewer adjustable split ring tubes 72, 74 may be provided, and rings 76, 78 may form different shapes than a ring. Build-up caps 94, 96, as illustrated, for example, in FIGS. 7 to 9, may be used to effectively space the radiation dose from its intended point of application.

Figure 7:
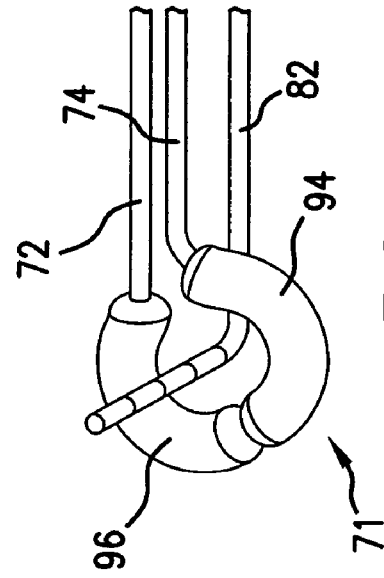
FIG. 7 is a perspective view of an end section of the split ring applicator illustrated in FIG. 6 including build-up caps.

FIG. 7 illustrates the distal end 71 of the split ring applicator 70 illustrated in FIG. 6. As illustrated in FIG. 7, the semi-circular rings 76, 78 of adjustable split ring tubes 72, 74 may include build-up caps 94, 96. Build-up caps 94, 96 may have a thickness of, e.g., between about 5 mm and about 7.5 mm but may also be provided in other sizes. Build-up caps 94, 96 may be reusable or disposable and may be made, for example, of moldable silicone rubber. However, other suitable materials may be utilized.

FIGS. 8 and 9 are plan views of the split ring applicator 70 illustrated in FIG. 6. FIG. 8 illustrates split ring applicator 70 in an open position and includes build-up caps 94, 96. As illustrated in FIG. 8, in the open position, outer surfaces of build-up caps 94, 96 as spaced laterally apart by a distance A. Distance A may be, e.g., approximately 80 mm to approximately 90 mm but may be tailored to specific clinical and/or anatomical conditions. Interface connections 92 and tandem interface connection 93 provide for connecting split ring applicator 70 to, e.g., an HDR afterloader. Interface connections 92 and tandem interface connection 93 may be compatible with all HDR afterloaders. The connectors 92, 93 may be identical, or each connector 92, 92, 93 may be different so that the connectors 92, 92, 93 are connectable only to a corresponding connector of the afterloader, e.g., to avoid misconnections to the afterloader. FIG. 9 illustrates split ring applicator 70 in a closed position and also includes build-up caps

94, 96. In the closed position, semi-circular rings 76, 78 essentially form a ring shape. Split ring applicator 70 may be locked in open or closed positions, or any position therebetween, by adjusting lock nuts 86 on adjustable brackets 88 of universal connecting joint 84. The split ring tubes 72, 74 of split ring applicator 70 are capable of being locked in varying open positions. For example, adjustable brackets 88 may provide for adjustment of adjustable split ring tubes 72, 74 in, e.g., approximately 5 mm increments. Other increments may be provided as appropriate.

FIG. 10 is a side view of the split ring applicator 70 illustrated in FIG. 9 without build-up caps 94, 96. Angled distal end section 83 of central tandem 82 forms angle θ with the axis of central tandem 82 which is essentially parallel to the axis of adjustable split ring tubes 72, 74. Angle θ may be, e.g., approximately 45° or may be provided in ranges between approximately 30° and approximately 60° but may also be provided at any desired custom angle and may be tailored to clinical and/or anatomical treatment conditions. Length L of angled end section 83 may be, e.g., between approximately 20 mm and approximately 80 mm but may also be provided in any desired custom length and may be tailored to clinical and/or anatomical treatment conditions. Additionally, the planar surface of semi-circular rings 76, 78 forms an angle β with the axis of adjustable split tubes 72, 74 which is essentially parallel to the axis of central tandem 82. Angle β may be, e.g., approximately 45° and maybe provided in ranges between, e.g., approximately 30° and approximately 60° but may also be provided at any desired custom angle and may be tailored to clinical and/or anatomical treatment conditions.

FIG. 11 is a plan view of a distal portion of the split ring applicator illustrated in FIG. 10. Distance B, between the outer surfaces of semi-circular rings 76, 78 may be, e.g., approximately 20 mm to approximately 40 mm but may be tailored to clinical and/or anatomical conditions. Thus, the ring formed by semi-circular rings 76, 78 of adjustable split ring tubes 72, 74 may be constructed of various diameter sizes and may be provided at various angles with respect to the axis of the adjustable split ring tubes 72, 74 as illustrated in FIG. 10.

Figure 12:
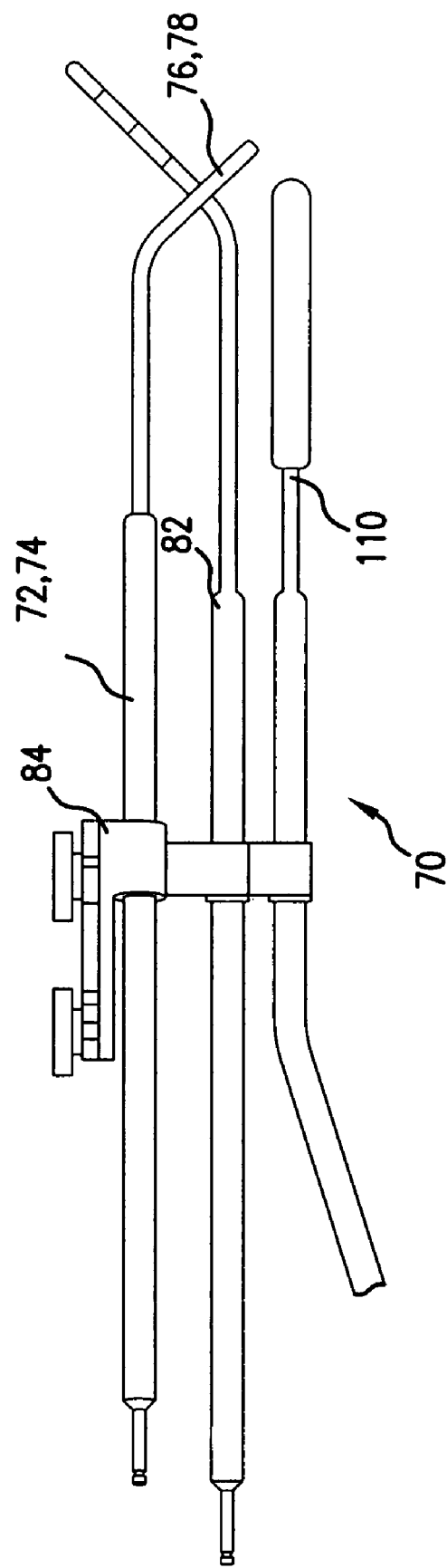
FIG. 12 is a side view of a split ring applicator according to an example embodiment of the present invention including a rectal retractor.

FIG. 12 is a side view of a split ring applicator 70 according to an example embodiment of the present invention. Split ring applicator 70 includes a rectal retractor 110. Rectal retractor 110 is attached to the split ring applicator 70 through universal connector 84. Rectal retractor 110 is inserted vaginally. Rectal retractor 110 may be adjusted to exert a force on a rectum and may be locked in place.

Split ring applicator 70 may be utilized for the treatment of cervical cancer by inserting the split ring applicator 70 in a cervix and adjusting lateral spacing of the adjustable split ring tubes 72, 74 in a lateral direction and then applying a radioactive treatment to a cervical wall from at least one of the adjustable split ring tubes 72, 74 by inserting a radioactive source, e.g., via an HDR afterloader, in at least one of the adjustable split ring tubes 72, 74. Split ring applicator 70 may be locked in an open position, as illustrated in FIG. 8, using lock nuts 86 of universal connector 84. Split ring applicator 70 may then be unlocked after the treatment time has passed and the split ring applicator 70 may be readjusted to reverse the adjustment of adjustable split ring tubes 72, 74 in a lateral direction and then split ring applicator 70 may be removed from the cervix.

Figure 13:
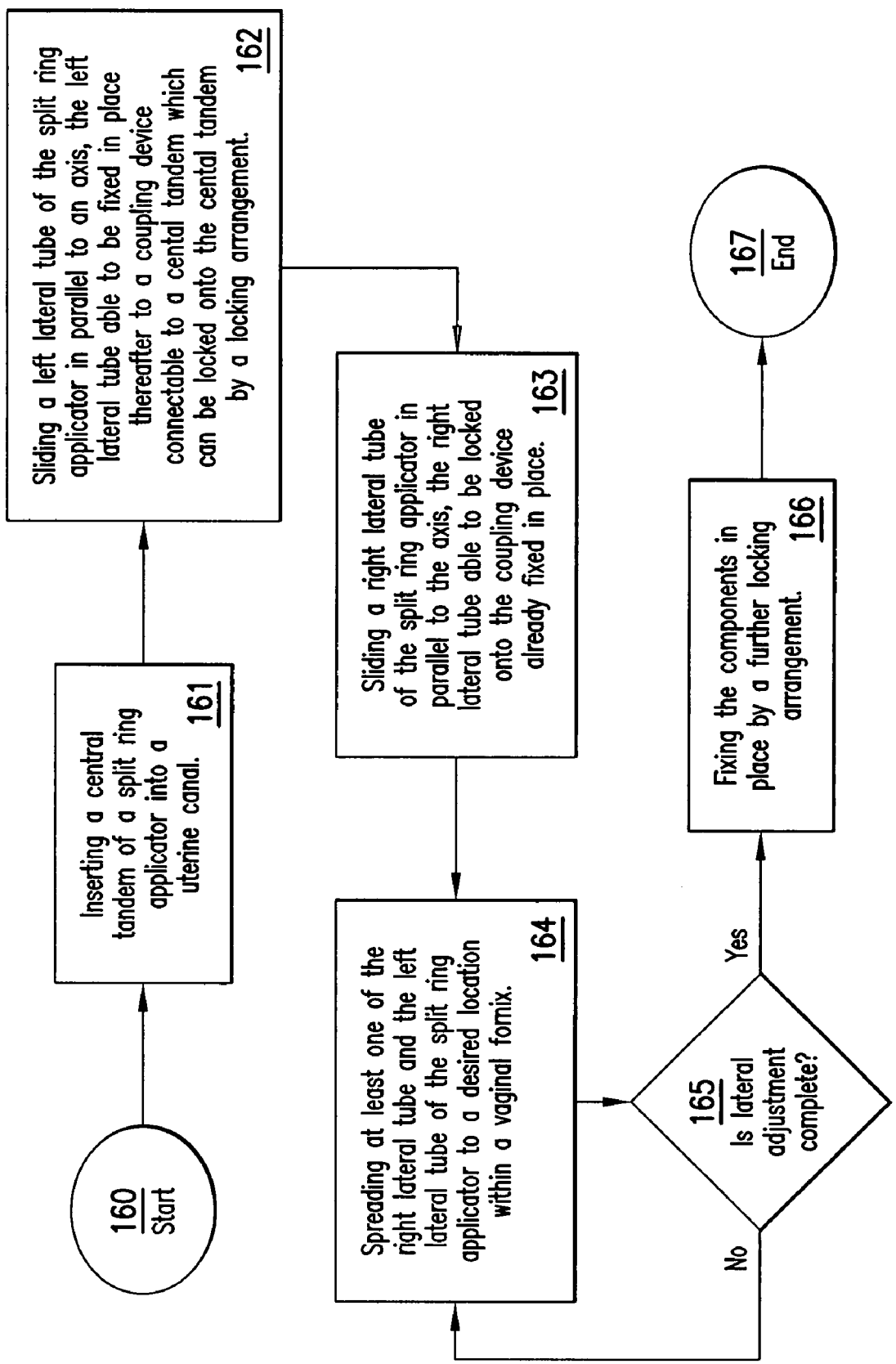
FIG. 13 is a flowchart illustrating a method of using a split ring cervical applicator, e.g., for treating cervical cancer.
Figure 14:
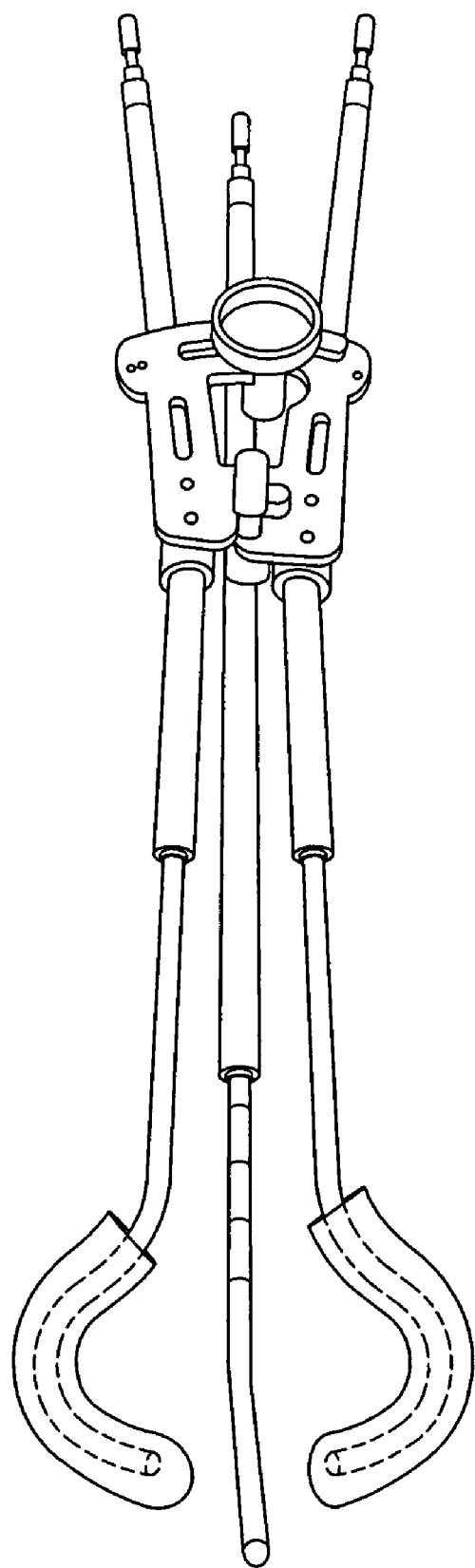
FIGS. 14 to 20 are photographs of an example embodiment of a split ring applicator.
Figure 15:
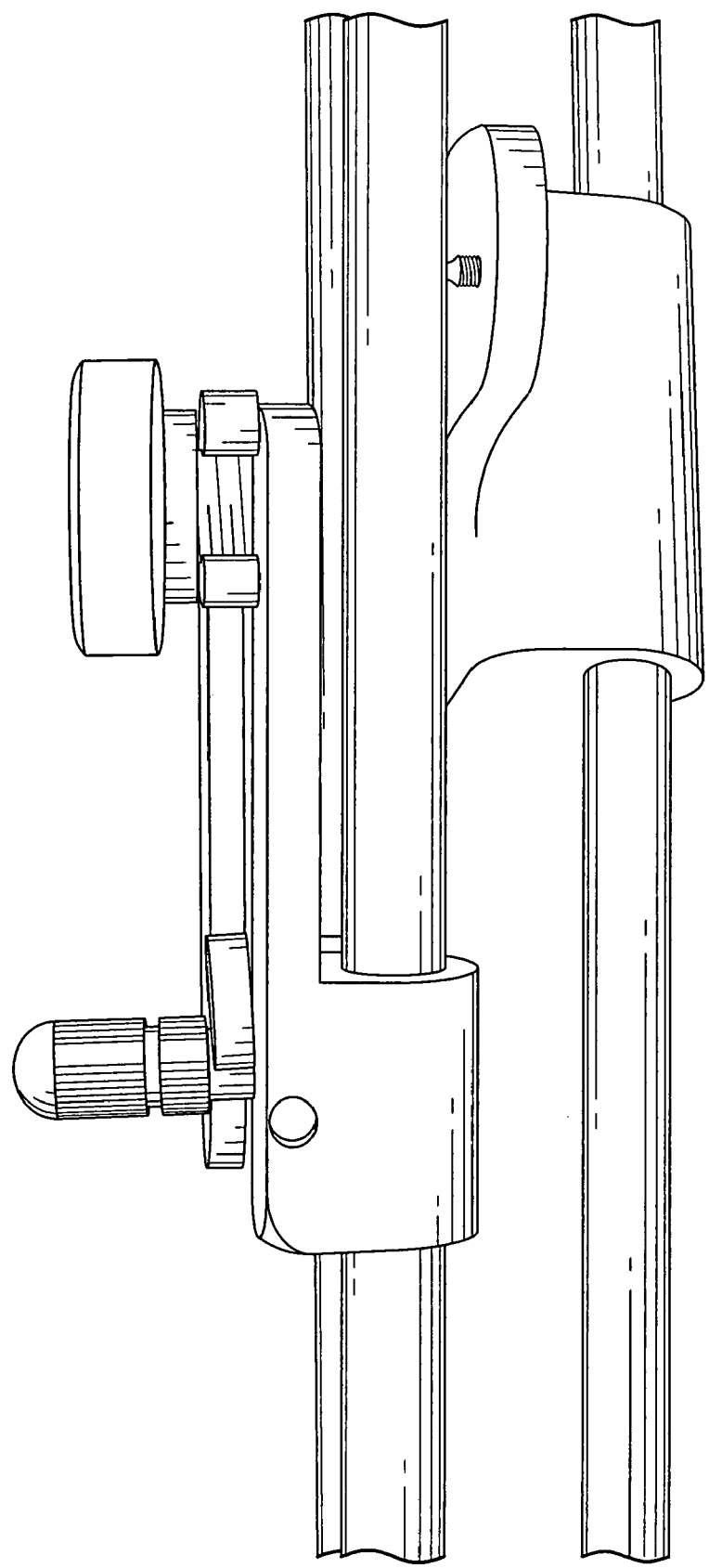
Figure 16:
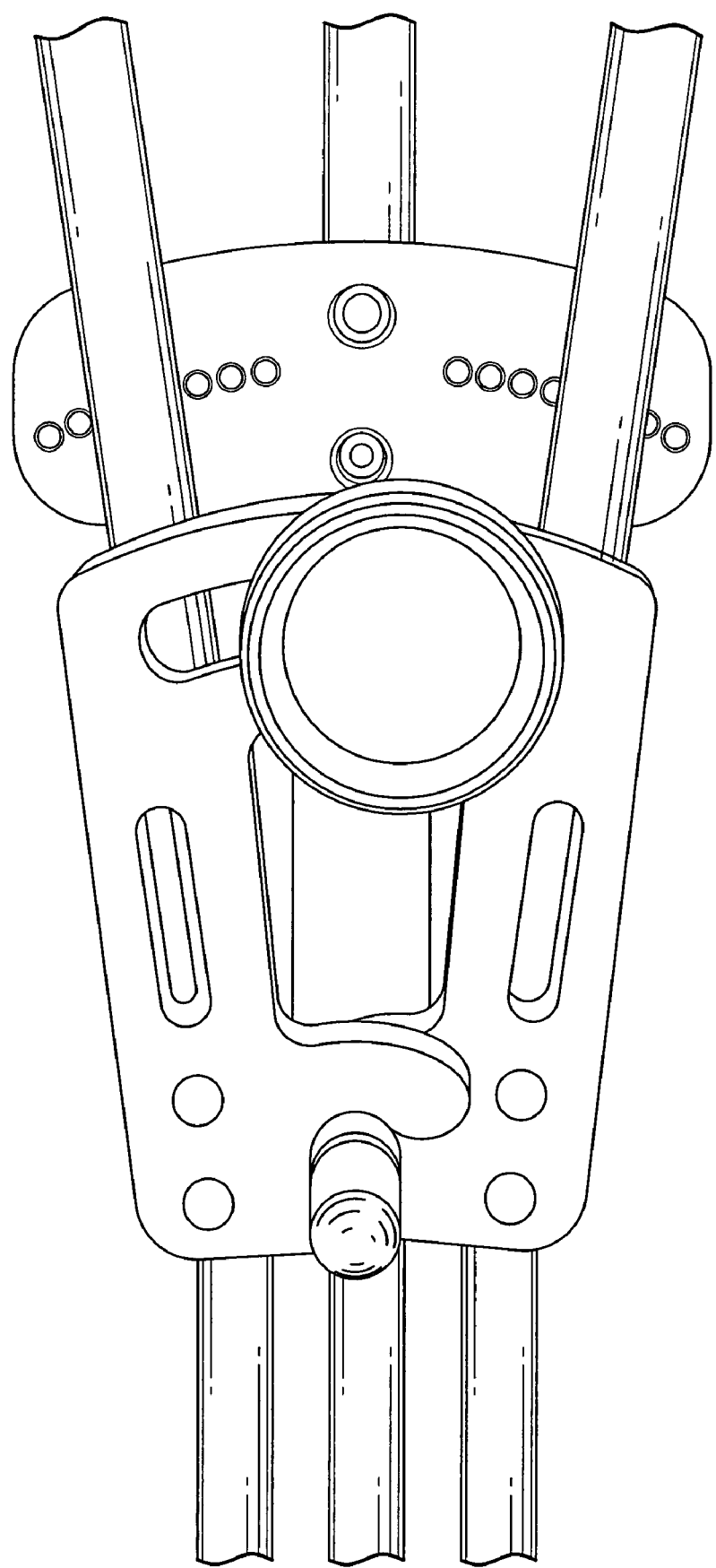
Figure 17:
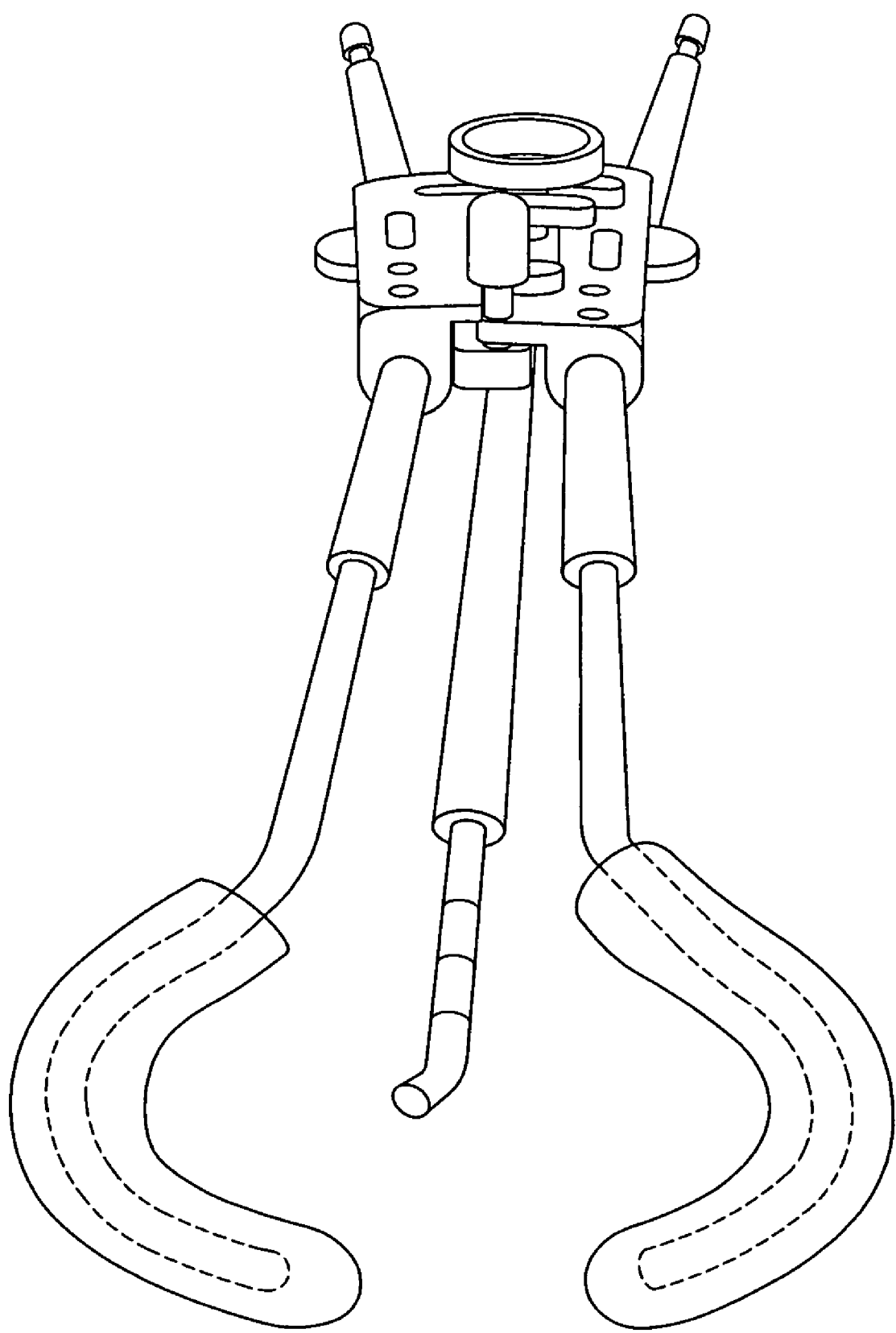
Figure 18:
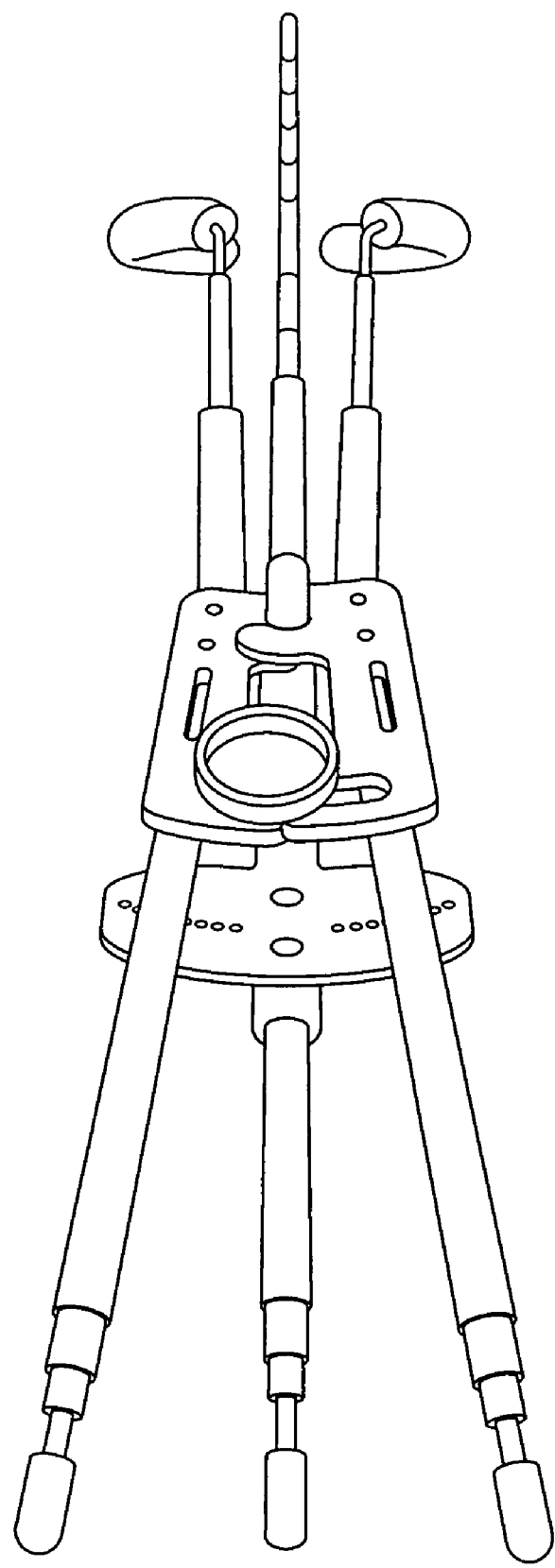
Figure 19:
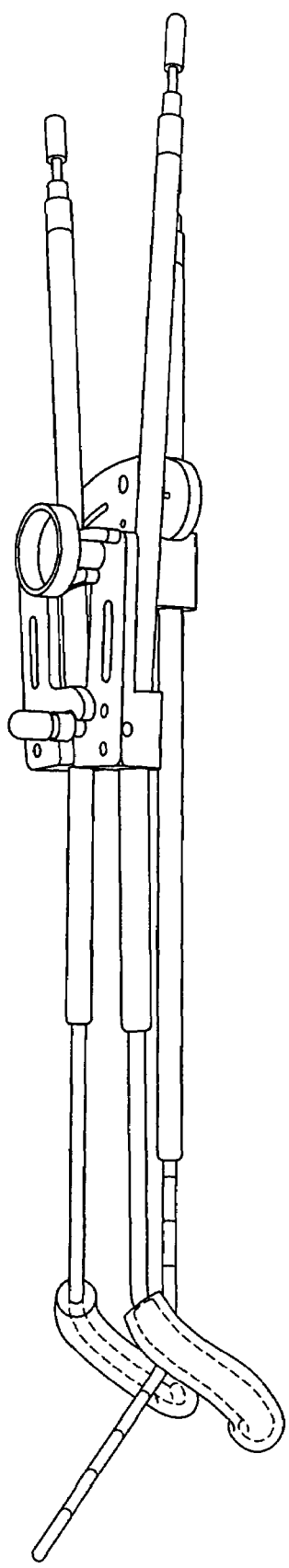
Figure 20:
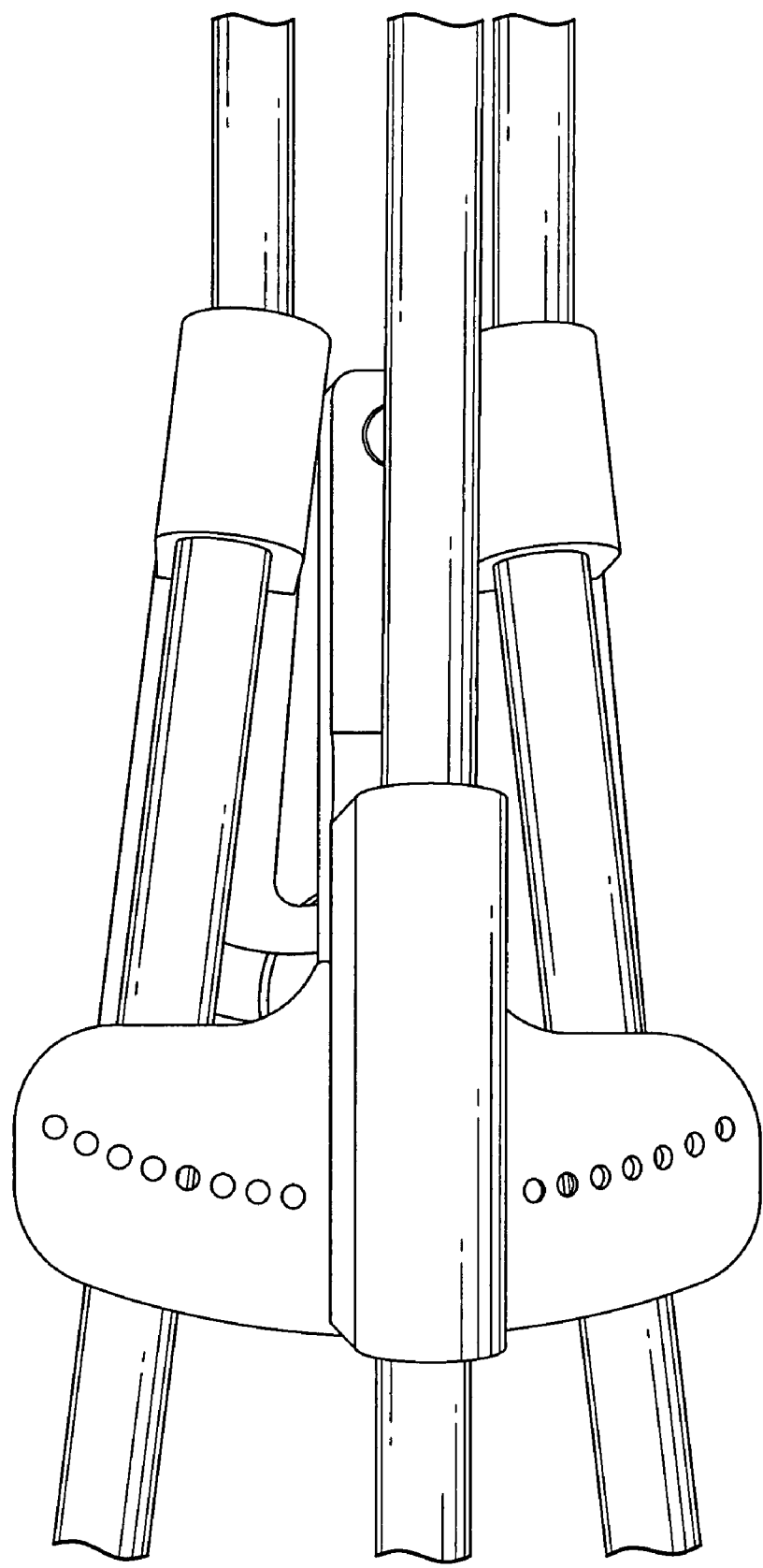

FIG. 13 is a flowchart illustrating a method of using a split ring cervical applicator for treating cancer according to an example embodiment of the present invention. The flow begins at 160 and proceeds to 161, which indicates to insert a central tandem of a split ring applicator into a uterine canal, the split ring applicator includes a plurality of lateral split ring tubes which are able to be spread within a vaginal fornix and tailored to clinical and anatomical treatment conditions. Next, the flow proceeds to 162, which indicates to slide a left lateral tube (left adjustable split ring tube) of the split ring applicator in parallel to an axis, the left lateral tube is able to be fixed in place thereafter to a coupling device connectable to the central tandem which may be locked onto the central tandem by a locking arrangement. Next, the flow proceeds to 163, which indicates to slide a right lateral tube (right adjustable split ring tube) of the split ring applicator in parallel to the axis, the right lateral tube is able to be locked onto the coupling device already fixed in place. Next, the method proceeds to 164, which indicates to spread at least one of the right lateral tube and the left lateral tube of the split ring applicator to a desired location within a vaginal fornix. The flow proceeds from 164 to 165, in which it is determined whether the lateral adjustment is complete. Many factors may influence this decision, including but not limited to, the size of the cervical cavity, the amount of pressure desired for the treatment, the type of treatment planned, etc. If it is determined in 165 that lateral adjustment is not complete, the flow returns to 164. However, if it is determined in 165 that lateral adjustment is complete, the method proceeds to 166, which indicates to fix all components in place by a further locking arrangement. The device may remain locked during the entire time of treatment. From 166, the method proceeds to end 167. In alternative methods, a "scissor-type" fixed and/or adjustable adjustable rectal retractor may be attached to the tandem and locked in place by a locking device.

Split ring applicator 70 may be constructed of materials commonly utilized in surgical devices including biocompatible alloys and thermoplastics. Metals such as aluminum, titanium, stainless steel, etc., may be used. For example, the components of split ring applicator 70 may be available in stainless steel with coated aluminum adjustable brackets 88. Alternatively, the components of split ring applicator 70 may be formed of titanium, a titanium alloy, or a thermoplastic or composite material. Split ring applicator 70 may be provided as CT/MR compatible. Split ring applicator 70 and/or its components may be provided in a sterilization cassette. Split ring applicator 70 may be "autoclaved" (steam sterilized) or autoclaveable, ETO sterilized (ethylene oxide) or sterilizable or other sterilization methods such as Gamma Sterilization (Sterrad) may also be used.

Split ring applicator 70 may be adapted for use with small and flexible HDR Ir-192 (High Dose Radiation—Iridium-192) sources, for example those sources manufactured by Varian, GammaMed and Nucletron.

The central tandem may be fixed centrally relative to the split tubes and/or the semi-circular rings, e.g., via the support bracket, e.g., so that the central tandem is always positioned centrally, i.e., the split tubes and/or semi-circular rings are always disposed symmetrically with respect to the central tandem when the device is in its assembled condition. In addition, the bracket may be adapted to fix the spread between the split tubes and/or semi-circular rings.

Annexed hereto as FIGS. 14 to 20 are photographs showing an example embodiment of the present invention.

FIG. 21 is a plan view of a split ring applicator 201 according to an example embodiment of the present invention. Split ring applicator 201 includes a central tandem 282 and a pair of adjustable split ring tubes, of which only one adjustable split ring tube 272 is illustrated in FIG. 21 for clarity. It should be appreciated that the adjustable split ring tubes of the split ring applicator 201 are substantially the same as the adjustable split ring tubes described above. As such, further description of the adjustable split ring tubes is not provided. The split ring applicator 201 includes a holder and pivot assembly 204, which is affixed to the central tandem 282 along the length of the central tandem 282. A pivot bracket 208 is affixed to each adjustable split ring tube 272 and pivotable about a pivot 206 of the holder and pivot assembly 204. A locking sleeve 210 is provided along the length of each adjustable split ring tube 272 and engaged with a tandem holder 214 of the holder and pivot assembly 204. A locking knob 212 is provided on the locking sleeve, e.g., threadedly, so that the adjustable split-ring tube 272 is pivotable about the pivot 206 and lockable in position relative to the central tandem 282. The pivot 206 may be threaded so that it may be tightened against the pivot bracket 208 to further secure the adjustable split ring tubes in position relative to each other and relative to the central tandem.

FIG. 22 is a side view of the split ring applicator illustrated in FIG. 21.

FIG. 23 is a cross-sectional view of the split ring applicator taken along the line A-A illustrated in FIG. 21. As illustrated in FIG. 23, the locking knob 212 may selectively engage a detent or bore 205a ... 205e, 207a ... 207e in the tandem holder 214 so that the adjustable split ring tubes may be selectively positioned in a predetermined position relative to each other and/or to the central tandem. The locking knob 212 may be directly engageable with the detent or bore, or a plunger 213, which may be spring loaded against the end of the locking knob, may be provided for engagement with the detent or bore.

Figure 24:
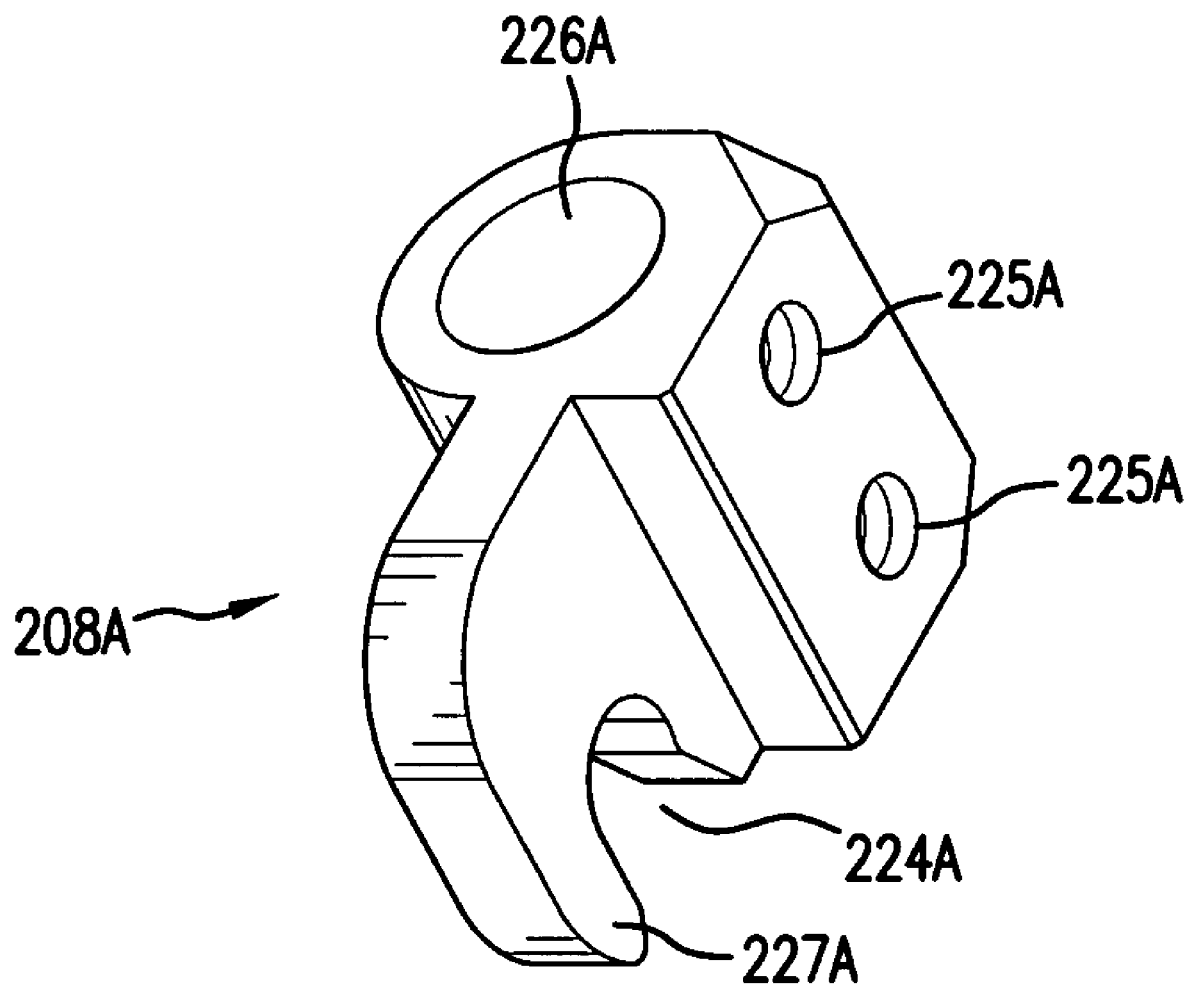
FIG. 24 is a perspective view of a pivot bracket of the split ring applicator illustrated in FIGS. 21 and 22.

FIG. 24 is a perspective view of a pivot bracket 208A, e.g., a left-side pivot bracket, of the split ring applicator 201 illustrated in FIGS. 21 and 22. The pivot bracket 208A includes a bore 226A, which receives the adjustable split ring tube 272, and a slot 224A in a tab 227A into which the pivot 206 is received. Threaded bores 225A, 225A are provided and receive set screws to secure the pivot bracket 208A to the adjustable split ring tube 272.

Figure 25:
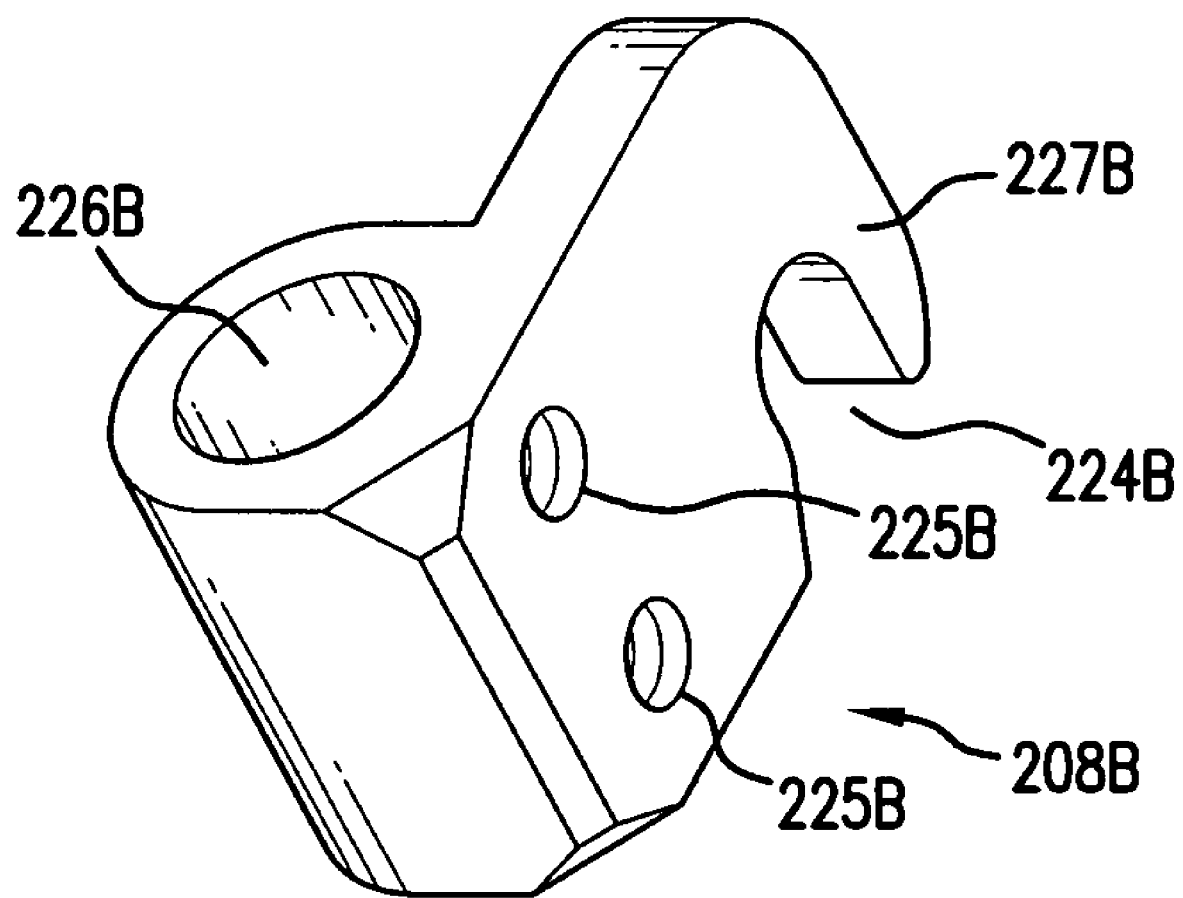
FIG. 25 is a perspective view of another pivot bracket of the split ring applicator illustrated in FIGS. 21 and 22.

FIG. 25 is a perspective view of another pivot bracket 208B, e.g., a right-side pivot bracket, of the split ring applicator 201 illustrated in FIGS. 21 and 22. The pivot bracket 208B includes a bore 226B, which receives the adjustable split ring tube 272, and a slot 224B in a tab 227B into which the pivot 206 is received. Threaded bores 225B, 225B are provided and receive set screws to secure the pivot bracket 208B to the adjustable split ring tube 272. The tabs 227A, 227B are staggered so that the tabs 227A, 227B are stacked when assembled and engaged with the pivot 206.

Figure 26:
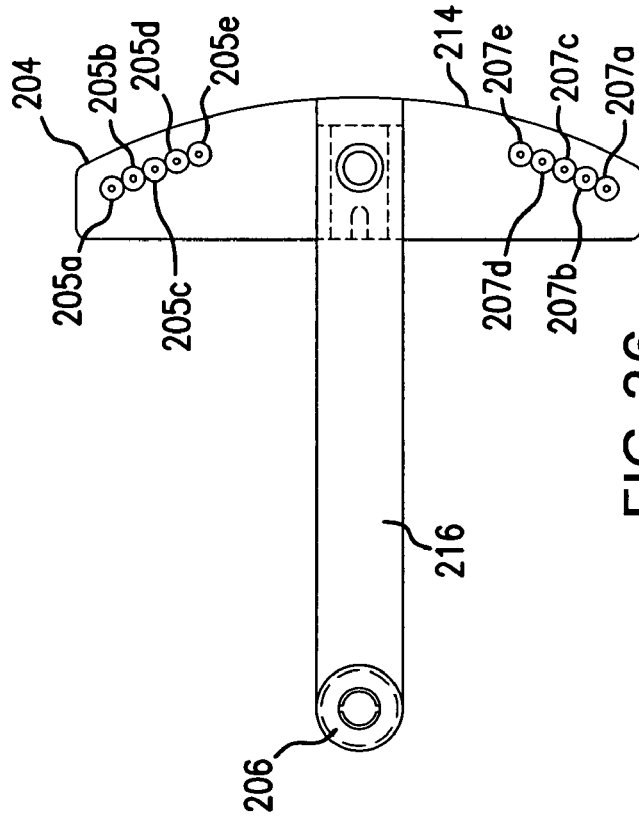
FIG. 26 is a plan view of a holder and pivot assembly of the split ring applicator illustrated in FIGS. 21 and 22.

FIG. 26 is a plan view of the holder and pivot assembly 214 of the split ring applicator 201 illustrated in FIGS. 21 and 22. The holder and pivot assembly 214 includes tandem holder 214 and pivot support 216. The pivot 206 is received in the pivot support 216. Tandem holder 214 includes a collar 220 having a bore 222 into which the central tandem 282 is received. The tandem holder 214 includes detents or bores 205a ... 205e, 207a ... 207e for locking the adjustable split ring tubes in predetermined positions relative to each other and/or to the central tandem 282. While five detents or bores are illustrated, it should be appreciated that any number of detents or bores may be provided as appropriate.

Figure 27:
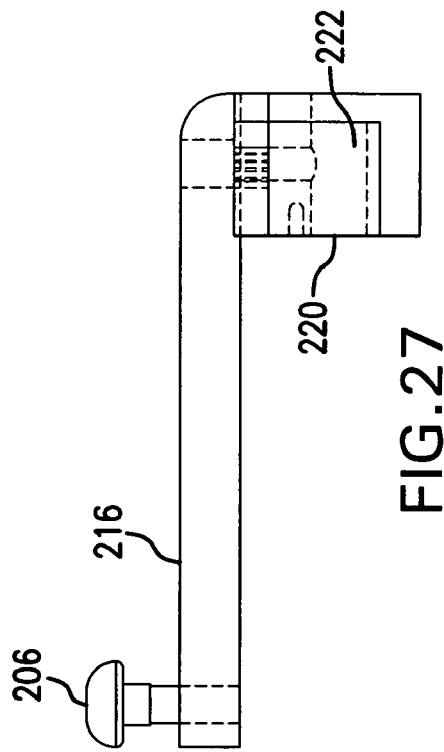
FIG. 27 is a side view of the holder and pivot assembly illustrated in FIG. 26.

FIG. 27 is a side view of the holder and pivot assembly 214 illustrated in FIG. 26.

Figure 28:
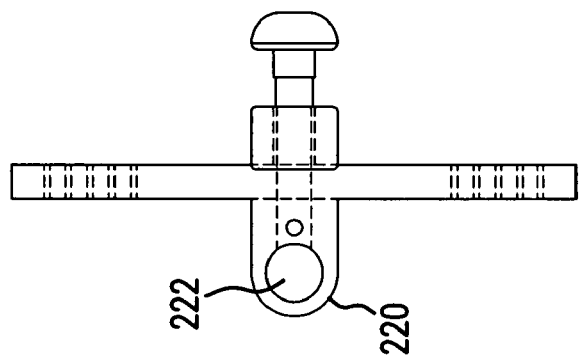
FIG. 28 is an end view of the holder and pivot assembly illustrated in FIG. 26.

FIG. 28 is an end view of the holder and pivot assembly 214 illustrated in FIG. 26.

Figure 29:
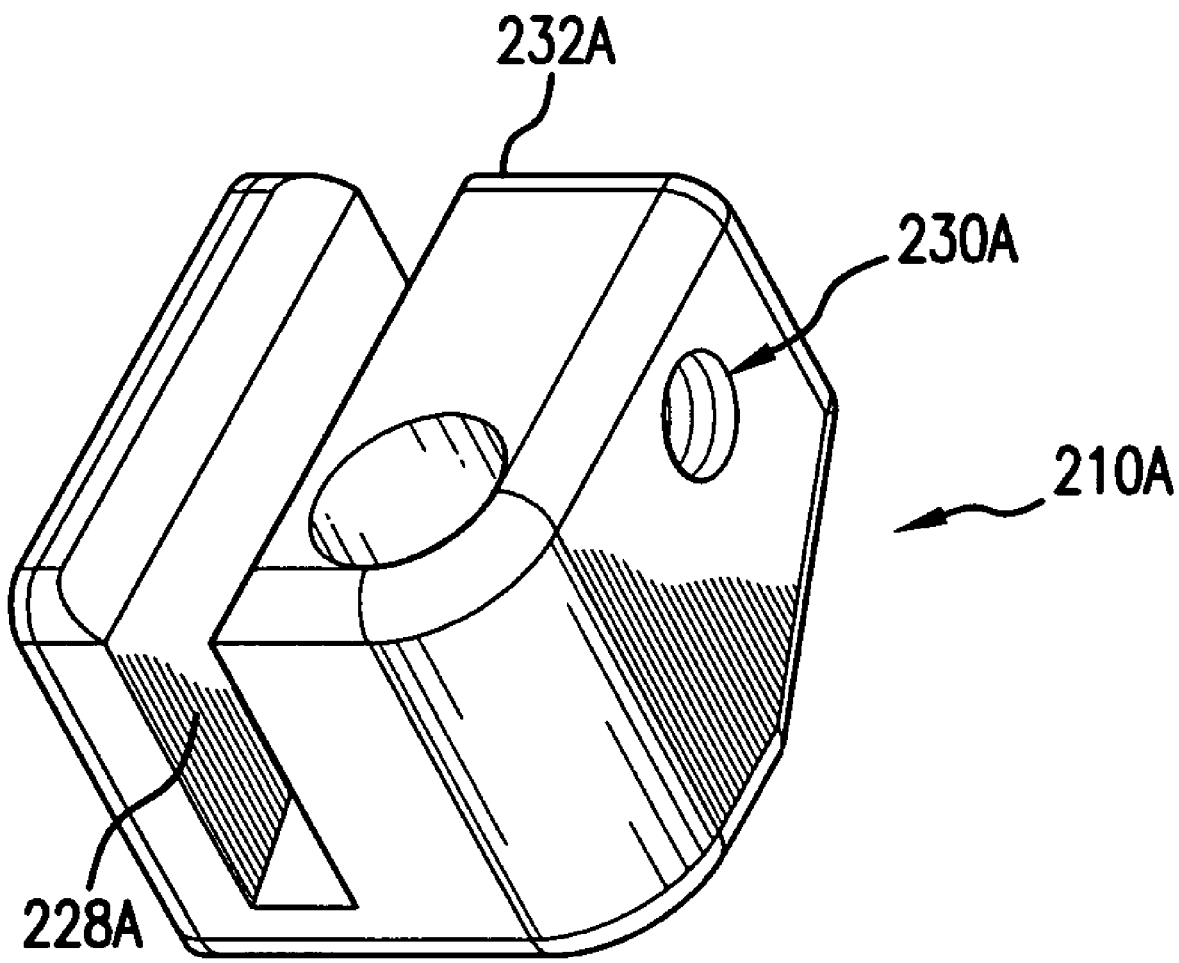
FIG. 29 is a perspective view of a locking sleeve of the split ring applicator illustrated in FIGS. 21 and 22.

FIG. 29 is a perspective view of a locking sleeve 210A, e.g., a right-side locking sleeve, of the split ring applicator 201 illustrated in FIGS. 21 and 22. The locking sleeve 210A includes a bore 232A for receiving the adjustable split ring tube 272 and a threaded bore 230A for receiving the locking knob 212 and/or plunger 213. A slot 228A is provided to receive the tandem holder 214.

Figure 30:
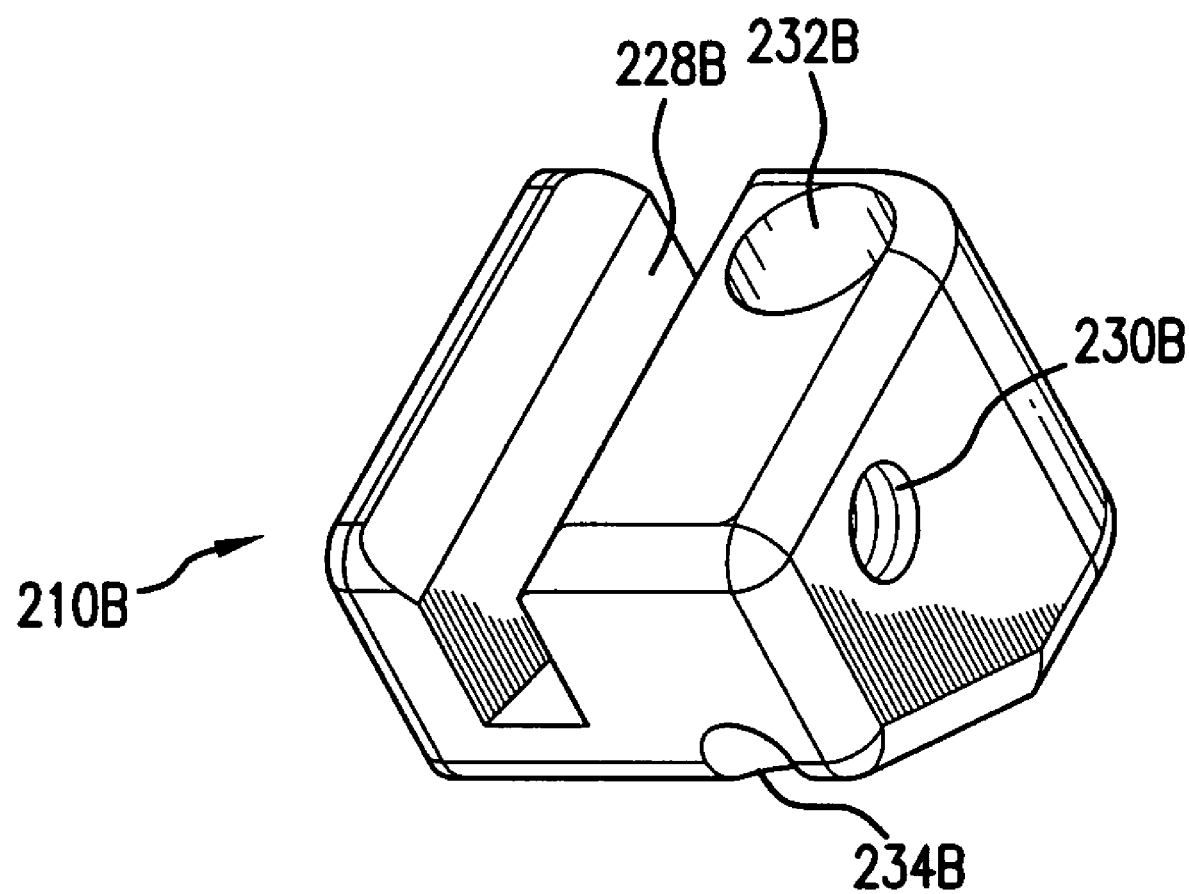
FIG. 30 is a perspective view of another locking sleeve of the split ring applicator illustrated in FIGS. 21 and 22.

FIG. 30 is a perspective view of another locking sleeve 210B, e.g., a left-side locking sleeve, of the split ring applicator 201 illustrated in FIGS. 21 and 22. The locking sleeve 210B includes a bore 232B for receiving the adjustable split ring tube 272 and a threaded bore 230B for receiving the locking knob 212 and/or plunger 213. A slot 228B is provided to receive the tandem holder 214. The locking sleeve 210B includes a threaded bore 234B for receiving a set screw to secure the locking sleeve 210B to the adjustable split ring tube 272. It should be appreciated that the locking sleeve 210A includes a corresponding threaded bore for receiving a set screw to secure the locking sleeve 210A to the adjustable split ring tube but that such a threaded bore is not visible in the view of FIG. 29. It should also be appreciated that locking sleeves 210A, 210B are mirror symmetric with respect to each other.

What is claimed is:

1. An applicator device, comprising:
    a plurality of split ring tubes adjustable laterally to a cervical axis, each split ring tube adapted to deliver a radiation dosage to a vaginal fornix; and
    a central tandem attached to the split ring tubes, the central tandem having a central axis arranged along the cervical axis between the plurality of split ring tubes;
    wherein each split ring tube includes a substantially straight proximal portion and generally semi-circular distal portion.

2. The device according to claim 1, further comprising a coupling device adapted to couple the split ring tubes and the central tandem.

3. The device according to claim 2, wherein the central tandem is rigidly attached to the coupling device.

4. The device according to claim 2, wherein the split ring tubes selectively lockable in position by the coupling device.

5. The device according to claim 1, further comprising a build-up cap disposed about a distal end of the split ring tube.

6. The device according to claim 5, wherein at least one of (a) the build-up caps have a thickness between about 5 mm and about 7.5 mm and (b) the build-up caps are formed of silicon rubber.

7. The device according to claim 1, wherein the distal portions of the split ring tubes form a substantially complete circular ring when the split ring tubes are in a closed position.

8. The device according to claim 7, wherein the ring has a diameter of between about 20 mm and about 40 mm.

9. The device according to claim 7, wherein the ring is disposed at an angle between about 30° and about 60° from a planar surface formed by a central axis of the ring tubes.

10. The device according to claim 1, wherein the central tandem has an angled distal end section, an angle of the angled distal end section between about 30° and about 60° from the central axis of the central tandem, the angled end section arranged approximately in a center of a ring formed by the semi-circular rings of the split ring tubes.

11. The device according to claim 10, wherein the angled distal end section of the central tandem has a length of between about 20 mm and about 80 mm.

12. The device according to claim 1, wherein the split ring tubes are laterally displaceable such that outer most surfaces of distal ends of the split ring tubes are at a distance of between about 60 mm and about 80 mm.

13. The device according to claim 1, further comprising a rectal retractor.

14. The device according to claim 1, wherein the applicator is at least one of (a) steam sterilizable, (b) ETO sterilizable and (c) gamma sterilizable.

15. The device according to claim 1, wherein a proximal end of each split ring tube includes a connector adapted to connect to a high dose rate afterloader device to deliver the radiation dosage into the split ring tube.

16. The device according to claim 1, wherein the plurality of split ring tubes are adjustable laterally symmetrically about the cervical axis.

17. The device according to claim 1, wherein the plurality of split ring tubes are adjustable laterally asymmetrically about the cervical axis.

18. A brachytherapy treatment system, comprising:
a split ring applicator including a plurality of split ring tubes adjustable laterally to a cervical axis, each split ring tube adapted to deliver a radiation dosage to a vaginal fornix, and a central tandem attached to the split ring tubes, the central tandem having a central axis arranged along the cervical axis between the plurality of split ring tubes; and
a high dose rate afterloader adapted to deliver the radiation dosage into at least one of the split ring tubes;
wherein each split ring tube includes a substantially straight proximal portion and generally semi-circular distal portion.

19. The system according to claim 18, wherein the high dose rate afterloader is adapted to deliver the radiation dosage into the central tandem.

20. The system according to claim 18, wherein the plurality of split ring tubes are adjustable laterally symmetrically about the cervical axis.

21. The system according to claim 18, wherein the plurality of split ring tubes are adjustable laterally asymmetrically about the cervical axis.

22. A method, comprising:
inserting a split ring applicator into a cervix, the applicator including a central tandem and a plurality of laterally adjustable split ring tubes;
adjusting a lateral spacing between the split ring tubes; and
applying a radioactive treatment to a vaginal fornix from the at least one of the split ring tubes;
wherein each split ring tube includes a substantially straight proximal portion and generally semi-circular distal portion.

23. The method according to claim 22, wherein the radioactive treatment is applied in the applying step to the vaginal fornix by inserting a radioactive source into at least one of the split ring tubes.

24. The method according to claim 22, further comprising locking the split ring tubes in a lateral spacing between the split ring tubes during a treatment time.

25. The method according to claim 24, further comprising:
unlocking the split ring tubes after the treatment time has elapsed;
reversing the adjustment of the split ring tubes in the lateral direction; and
removing the split ring applicator from the cervix.

26. The method according to claim 22, further comprising:
attaching an adjustable rectal retractor to the split ring applicator;
retracting a rectum away from the split ring tubes by the rectal retractor; and
locking the rectal retractor in place after the retracting step.

27. The method according to claim 22, wherein in the adjusting step, the split ring tubes are adjusted to a symmetric lateral spacing.

28. The method according to claim 22, wherein in the adjusting step, the split ring tubes are adjusted to an asymmetric lateral spacing.

29. A method, comprising:
inserting a central tandem of a split ring applicator into a uterine canal, the split ring applicator including at least a first split ring lateral tube and a second split ring lateral tube, the first split ring lateral tube and the second split ring lateral tube spreadable within at least one vaginal fornix;
sliding the first split ring lateral tube of the split ring applicator in a direction substantially parallel to an axis of the central tandem, the first split ring lateral tube fixable in place thereafter to a coupling device, the coupling device connectable to the central tandem and lockable onto the central tandem by a first locking arrangement;
sliding the second split ring lateral tube of the split ring applicator in a direction substantially parallel to the axis of the central tandem, the second split ring lateral tube lockable onto the coupling device;
spreading at least one of the first split ring lateral tube and the second split ring lateral tube of the split ring applicator to a desired location within the at least one vaginal fornix; and
fixing the at least one of the first split ring lateral tube and the second split ring lateral tube in place by a second locking arrangement;
wherein each split ring tube includes a substantially straight proximal portion and generally semi-circular distal portion.

30. The method according to claim 29, wherein at least one of (a) the first split ring lateral tube and (b) the second split ring lateral tube is adapted to at least one of (a) a clinical condition and (b) an anatomical treatment condition.

31. The method according to claim 29, wherein in the spreading step, the at least one of the first split ring lateral tube and the second split ring lateral tube are spread symmetrically.

32. The method according to claim 29, wherein in the spreading step, the at least one of the first split ring lateral tube and the second split ring lateral tube are spread asymmetrically.

* * * * *